(12) United States Patent
Madabhushi et al.

(10) Patent No.: US 10,575,774 B2
(45) Date of Patent: Mar. 3, 2020

(54) PREDICTING IMMUNOTHERAPY RESPONSE IN NON-SMALL CELL LUNG CANCER WITH SERIAL RADIOMICS

(71) Applicant: Case Western Reserve University, Cleveland, OH (US)

(72) Inventors: Anant Madabhushi, Shaker Heights, OH (US); Yuanqi Xie, Cleveland, OH (US); Vamsidhar Velcheti, Pepper Pike, OH (US)

(73) Assignee: Case Western Reserve University, Cleveland, OH (US)

( * ) Notice: Subject to any disclaimer, the term of this patent is extended or adjusted under 35 U.S.C. 154(b) by 33 days.

(21) Appl. No.: 15/853,133

(22) Filed: Dec. 22, 2017

(65) Prior Publication Data

US 2018/0247410 A1    Aug. 30, 2018

Related U.S. Application Data

(60) Provisional application No. 62/464,007, filed on Feb. 27, 2017.

(51) Int. Cl.
*G06T 7/11* (2017.01)
*G06T 7/33* (2017.01)
(Continued)

(52) U.S. Cl.
CPC ........ *A61B 5/4839* (2013.01); *A61B 5/02007* (2013.01); *A61B 5/4848* (2013.01);
(Continued)

(58) Field of Classification Search
None
See application file for complete search history.

(56) References Cited

U.S. PATENT DOCUMENTS 5,762,921 A     6/1998  Vehar
2010/0254589 A1  10/2010  Gallagher
(Continued)

OTHER PUBLICATIONS

U.S. Appl. No. 15/893,086, filed Feb. 9, 2018.
Notice of Allowance dated May 23, 2019 in connection with U.S. Appl. No. 15/893,086.

*Primary Examiner* — Idowu O Osifade
(74) *Attorney, Agent, or Firm* — Eschweiler & Potashnik, LLC

(57) ABSTRACT

One embodiment include an image acquisition circuit that accesses a pre-treatment and a post-treatment image of a region of tissue demonstrating non-small cell lung cancer (NSCLC), a segmentation and registration circuit that annotates the tumor represented in the images, and that registers the pre-treatment image with the post-treatment image; a feature extraction circuit that selects a set of pre-treatment and a set of post-treatment radiomic features from the registered image; a delta radiomics circuit that generates a set of delta radiomic features by computing a difference between the set of post-treatment radiomic features and the set of pre-treatment radiomic features; and a classification circuit that generates a probability that the region of tissue will respond to immunotherapy based on the difference, and that classifies the region of tissue as a responder or non-responder. Embodiments may generate an immunotherapy treatment plan based, at least in part, on the classification.

29 Claims, 8 Drawing Sheets

(51) Int. Cl.
- *G06T 7/00* (2017.01)
- *G06K 9/62* (2006.01)
- *G16H 30/40* (2018.01)
- *A61B 6/00* (2006.01)
- *A61B 5/02* (2006.01)
- *G06T 7/174* (2017.01)
- *G16H 50/30* (2018.01)
- *G16H 50/20* (2018.01)
- *G16H 50/50* (2018.01)
- *A61K 49/00* (2006.01)
- *G06K 9/46* (2006.01)
- *A61B 5/00* (2006.01)
- *A61B 6/03* (2006.01)
- *A61B 5/055* (2006.01)

(52) U.S. Cl.
CPC .............. *A61B 5/7267* (2013.01); *A61B 6/50* (2013.01); *A61K 49/0004* (2013.01); *G06K 9/46* (2013.01); *G06K 9/6256* (2013.01); *G06K 9/6267* (2013.01); *G06K 9/6269* (2013.01); *G06K 9/6277* (2013.01); *G06K 9/6284* (2013.01); *G06T 7/0014* (2013.01); *G06T 7/0016* (2013.01); *G06T 7/11* (2017.01); *G06T 7/174* (2017.01); *G06T 7/337* (2017.01); *G16H 30/40* (2018.01); *G16H 50/20* (2018.01); *G16H 50/30* (2018.01); *G16H 50/50* (2018.01); *A61B 5/055* (2013.01); *A61B 5/4842* (2013.01); *A61B 5/7264* (2013.01); *A61B 6/032* (2013.01); *G06K 2209/05* (2013.01); *G06T 2200/04* (2013.01); *G06T 2207/10081* (2013.01); *G06T 2207/20076* (2013.01); *G06T 2207/20081* (2013.01); *G06T 2207/20084* (2013.01); *G06T 2207/30024* (2013.01); *G06T 2207/30061* (2013.01); *G06T 2207/30064* (2013.01); *G06T 2207/30096* (2013.01); *G06T 2207/30101* (2013.01)

(56) References Cited

U.S. PATENT DOCUMENTS

| | | |
|---|---|---|
| 2010/0303714 A1 | 12/2010 | Kim |
| 2011/0181614 A1 | 7/2011 | Chang |
| 2011/0318430 A1 | 12/2011 | Meruelo |
| 2013/0329973 A1 | 12/2013 | Cao |
| 2015/0254840 A1* | 9/2015 | Madabhushi ......... G06T 7/0012 382/131 |
| 2016/0220711 A1 | 8/2016 | DeMore |

* cited by examiner

PREDICTING IMMUNOTHERAPY RESPONSE IN NON-SMALL CELL LUNG CANCER WITH SERIAL RADIOMICS

CROSS REFERENCE TO RELATED APPLICATIONS

This application claims the benefit of U.S. Provisional Application 62/464,007 filed Feb. 27, 2017.

BACKGROUND

PD-L1 inhibitors are a group of drugs that inhibit the interaction between programmed death-ligand 1 (PD-L1) with its receptor, programmed cell death protein 1 (PD-1). This pathway, once activated, is a mechanism for tumor escape by T-cell exhaustion. Inhibition of this pathway is one approach to treating cancer. Nivolumab, a human IgG4 anti-PD-1 monoclonal antibody, works as an immune checkpoint inhibitor that blocks this pathway. Nivolumab is used as treatment of chemotherapy refractory advanced non-small cell lung cancer (NSCLC). As immunotherapy agents, such as nivolumab, become more widely used in treating NSCLC, medical practitioners face a challenge in the evaluation of the clinical efficacy of such immunotherapy agents.

There are no standard guidelines for evaluating response to treatment with PD-L1 checkpoint inhibitors such as nivolumab. In clinical practice, conventional radiological tools, including Response Evaluation Criteria in Solid Tumors (RECIST), have been employed. The RECIST criteria consider a significant increase in the size of tumor lesions and the development of new lesions to be unequivocal disease progression. Conventional approaches such as the RECIST criteria are used as operational thresholds that mandate the cessation of current therapy and the initiation of an alternate therapeutic regime. However, these conventional approaches that take into account the widest diameter of the tumor, have underestimated the benefit of therapy to patients because of the increase in tumor dimensions in patients who otherwise responded favorably to the treatment.

Such patients may be referred to as "pseudoprogressors". Some patients respond to immunotherapy with tumor shrinkage or stable disease and are thus more likely to be accurately characterized by the RECIST criteria. However, pseudoprogressors may exhibit distinct immune-related patterns of response, including new lesions associated with edema, infiltrates of immune cells, and transient increases in baseline tumor lesions. Delayed clinical responses to immunotherapeutic agents may also be observed, resulting in an initial increase in total tumor burden which is then followed by tumor regression. These pseudoprogressor findings would be misclassified by conventional approaches as progressive disease, which may lead to poor patient outcomes because treatment that would be helpful is mischaracterized as ineffective. Additionally, positron emission tomography (PET) also shows false positives because of the activation of T-cells against cancer cells, which may lead to uptake of fluorodeoxyglucose (FDG). Thus, conventional approaches to predicting patient response to immunotherapy are not optimal.

BRIEF DESCRIPTION OF THE DRAWINGS

The accompanying drawings, which are incorporated in and constitute a part of the specification, illustrate various example apparatus, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that, in some examples, one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Figure 1:
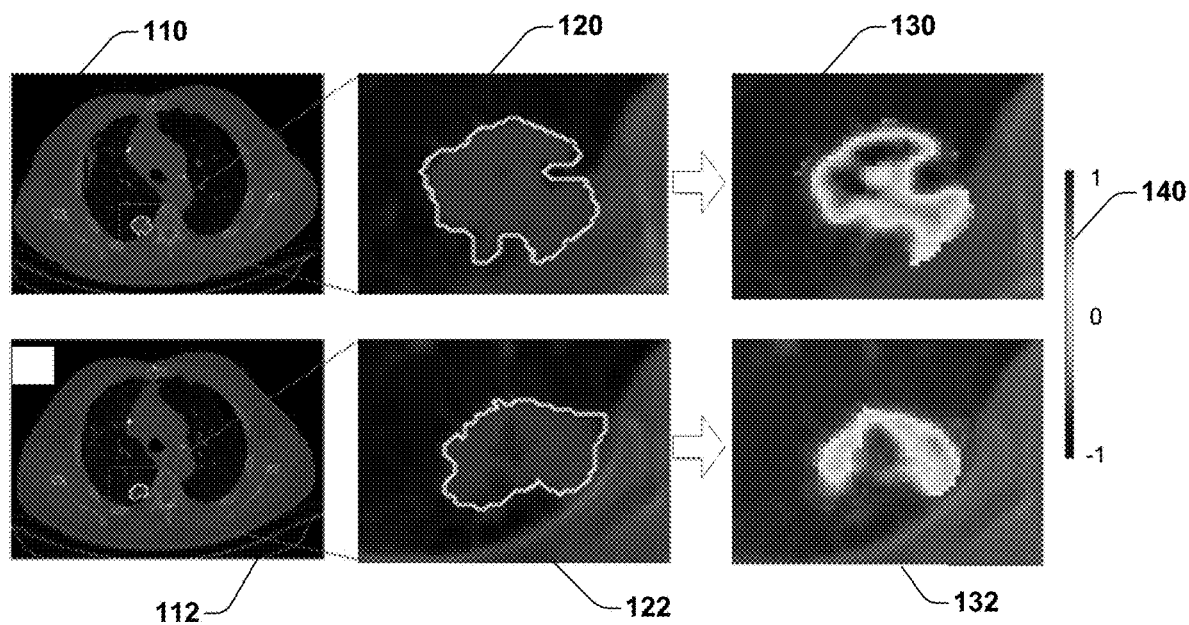
FIG. 1 illustrates segmented NSCLC tumor regions and a heatmap in pre-treatment and post-treatment computed tomography (CT) images.

Embodiments described herein use computer extracted measurements of quantitative imaging features that significantly and differentially change post treatment between NSCLC patients who do and do not respond to immunotherapy to predict patient response to immunotherapy. While one embodiment described herein predicts NSCLC patient response to nivolumab immunotherapy, other embodiments may predict patient response to other types of immunotherapy, or for other types of cancer, including breast cancer, head and neck cancer, bladder cancer, prostate cancer, rectal cancer, melanoma, brain cancer including Glioblastoma, or other types of cancer. Example embodiments directly transform a CT image of lung tissue into a probability of a patient-level response to immunotherapy. Example methods and apparatus automatically and reproducibly quantify the probability that a patient will respond to immunotherapy. Example methods and apparatus use automated computational radiomic image analysis to generate a patient-level prediction of response to immunotherapy based on differences between sub-visual features extracted from baseline pre-treatment CT imagery and post-treatment CT imagery with an accuracy of at least 78%. The sub-visual features extracted from CT imagery are more than volumetric measurements, and characterize the biology of the disease. These sub-visual characteristics thus serve as a biomarker to predict treatment response and to visualize disease processes in a non-invasive manner. Example methods and apparatus are more accurate in predicting patient response to immunotherapy than conventional computer assisted approaches, and are also more accurate than expert human pathologists.

Embodiments described herein may train, test, and employ a machine learning classifier, including a support vector machine (SVM), to predict patient response to immunotherapy from digitized CT images of lung tissue. Example methods and apparatus automatically and reproducibly predict patient response to immunotherapy based on baseline and post-treatment imagery because the computed difference in features between the baseline and post-treatment CT images, and the machine learning classifier, are deterministic and will repeatedly produce the same classification on the same input sample. This is in contrast to human experts that exhibit inter-expert and intra-expert variances. Automated analysis and grading of baseline and post-treatment CT imagery as described herein may further be employed as an objective second read of human radiologists or oncologists to improve NSCLC treatment, including the application of immunotherapy. Example embodiments support personalized medicine and precision medicine initiatives to enhance the targeting of therapeutics based on the deeper understanding of disease mechanisms and their manifestations within individual patients provided by example embodiments.

In one embodiment, CT images from a cohort of patients who were treated with nivolumab over a 34 month period were acquired. All patients in the cohort underwent baseline, pre-treatment CT imaging before starting treatment with nivolumab. For a patient, after four doses of nivolumab, where each dose was administered two weeks apart, a follow up CT scan was acquired at each two-week interval. In this embodiment, forty-eight patients in the cohort who underwent treatment with nivolumab were divided into a group of responders and a group of non-responders. Patients who did not receive nivolumab treatment after two cycles due to lack of response or to disease progression were classified as non-responders. Disease progression in this embodiment is defined as at least a 20% increase in the sum of diameters of target lesions, as per RECIST v1.1. Patients who experienced radiological response, including complete response (CR), and non-CR/non-progressive disease (PD), as per RECIST v1.1, or stable disease, as per RECIST v.1.1, or who experienced clinical improvement, were classified as responders. In this embodiment, CR is defined as the disappearance of all non-target lesions and normalization of tumor marker level. Non-CR/non-PD is defined as persistence of one or more non-target lesions or maintenance of tumor marker level above standard limits. In this embodiment, the cohort was divided into a training cohort of 22 patients, and a testing cohort of 26 patients that was held out and used as a blinded validation set.

In this embodiment, lung nodules on the pre-treatment CT images and post-treatment CT images are annotated using three dimensional (3D) Slicer software by an expert human radiologist. Annotating a lung nodule may include segmenting the nodule from the background of the image. In another embodiment, lung nodules may be annotated using other techniques, included automated segmentation techniques. Post-treatment CT images were then co-registered to pre-treatment CT images. In one embodiment, the post-treatment images were co-registered to the pre-treatment CT images using an Elasitx registration tool, while in another embodiment, other registration techniques may be employed. Co-registration ensures that acquired CT scans for a patient at different time points are registered to the baseline CT image. In this embodiment, affine registration is employed, while in other embodiments, other registration techniques may be used. Registration may be manually adjusted by an expert human radiologist, or may be adjusted automatically.

Example embodiments extract radiomic features from the registered baseline pre-treatment CT image and the post-treatment CT image or images. A CT image has a plurality of voxels. A voxel has an intensity value. In this embodiment, radiomic features are quantitative image features extracted from the information contained in voxels in the CT imagery. Radiomic features may be used for quantitative prediction or prognostic purposes in cancer diagnostics or in generating a cancer treatment plan for a patient. Radiomic features include statistical features, texture features, shape features, or other quantitative image features extracted from the information contained in voxels in the CT imagery. Radiomic features are extracted from the segmented nodule. Embodiments may generate a histogram of voxel intensities. In one embodiment, radiomic features may include first order statistics derived from a histogram of voxel intensities. These statistics reflect the mean value, standard deviation, skewness or kurtosis which describe asymmetry and sharpness, respectively. These statistics may also reflect uniformity, such as entropy. Texture features, based on different parent matrices, capture a spatial intensity distribution. In this embodiment, texture features reflect higher order statistical measures and may summarize the local spatial arrangement of intensities. Shape features describe the 3D geometrical composition of the segmented nodule structure. Shape features may include size measures, such as volume, perimeter, diameter, or other size measures. Shape features may include shape measures, including sphericity, compactness, radial distance, or other shape measures.

Embodiments described herein select radiomic features that achieve at least a threshold level of discriminability in characterizing a region of tissue as a responder or non-non-responder. Embodiments described herein may also select radiomic features based on a level of stability between baseline pre-treatment imagery and post-treatment imagery. For example, embodiments described herein may select features based on a threshold level of reliability and a threshold level of reproducibility between baseline pre-treatment imagery and post-treatment imagery. In one embodiment, radiomic features include a total of 312 texture features and 22 shape features automatically extracted from annotated nodules. The texture features include a Gray feature, a Gradient feature, a Haralick feature, a Gabor feature, and a Laws feature. Extracted radiomics features are then normalized to adjust values to a notionally common scale between −1 and 1. Embodiments described herein further compute a percent difference of feature intensity values between pre-treatment imagery and post-treatment imagery, and select these serial or delta radiomic features that are highly discriminative between responders and non-responders based on the computed difference.

Embodiments described herein may select radiomic features using a feature selection approach selected from among different feature selection approaches. Different feature selection approaches include a T-test score method, a Wilcoxon rank sum method, or a minimum redundancy maximum relevancy (mRMR) approach. A first feature selection approach may select different radiomic features from the same image than a second, different feature selection approach. For example, a T-test score feature selection approach may select a Gray feature, a Wilcoxon rank sum feature selection approach may select an L5R5L5 Laws feature, while an mRMR feature selection approach may select a Sobel y gradient feature. In a preferred embodiment, an mRMR feature selection approach is employed.

Embodiments described herein employ a machine learning classifier to characterize a region of tissue as a responder or non-responder using the selected delta radiomics features. The machine learning classifier may be a supervised learning classifier which learns from labeled training samples. Labeled training samples may include the images acquired from the training cohort of 22 patients, and the testing cohort of 26 patients that was used as a blinded validation set.

Embodiments described herein, to more effectively train the machine learning classifier to accurately characterize a region of tissue as a responder or non-responder, may identify and remove outlier cases from the training and testing cohorts. In one embodiment, selecting outliers involves three steps. In a first step, in an unsupervised clustering step, the top six most discriminative features are selected from the images acquired from the training cohort of 22 patients, and the testing cohort of 26 patients. The top three of those top six features are used to generate two 3D plots: a first 3D plot of the training cohort of 22 patients and a second, different 3D plot the testing cohort of 26 patients. In a second step, in the first 3D plot and the second 3D plot, the distance between each two samples is calculated. In one embodiment, an L2 norm is calculated to compute distance between the delta radiomic measurements. In a third step, samples that have relatively larger distances are selected as the outliers. In one embodiment, a threshold based on assumptions of normality and 95% confidence intervals is used to select outliers. In this embodiment, any sample that falls outside 2 standard deviations of the mean value is deemed an outlier and eliminated. Thus, in one embodiment, one sample is removed from the training cohort, and three samples are removed from the testing cohort. Training the machine learning classifier with a training dataset that has the outliers removed results in improved accuracy of classification compared to approaches that do not remove outliers. Furthermore, reducing the number of samples used to train the classifier, while improving accuracy, also increases the speed with which the classifier may be trained. While in this example, eliminating outliers includes three steps, in another embodiment, outliers may be eliminated using other, different techniques or numbers of steps.

The machine learning classifier may be a discriminant analysis (DA) machine learning classifier, a nearest neighbor (NN) machine learning classifier, a random forest (RF) machine learning classifier, or a support vector machine (SVM). A DA machine learning classifier may be a linear discriminant analysis (LDA) classifier, or a quadratic discriminant analysis (QDA) classifier. In one embodiment, the SVM classifier may have three kernels, including a linear kernel, a radial basis function (RBF) kernel, and a polynomial kernel. In another embodiment, the machine learning classifier may employ a convolutional neural network (CNN).

Embodiments described herein may select radiomic features based on a level of stability between baseline pre-treatment imagery and post-treatment imagery using a texture feature concordance approach. Example embodiments may employ a concordance correlation coefficient (CCC) to evaluate the reproducibility and reliability between features extracted from a pre-treatment CT image and a post-treatment CT image acquired from the same patient. In one embodiment, a CCC value of 0.8 is used as a threshold to assess reproducibility of the radiomic feature. A radiomic feature with a CCC value greater than 0.8 is considered a reproducible feature. To further ensure stability of radiomic features, after classification of the training set, the six top ranked features were selected. Using the Reference Image Database to Evaluate Therapy Response (RIDER) dataset of CT images of patients demonstrating NSCLC, the CCC value for the six top ranked features may be calculated. While a CCC value of 0.8 is described, other CCC values may be employed, and other conditions, such as a CCC value greater than or equal to (>=) the threshold value may be employed. By selecting radiomic features based, in part, on the stability of the feature as represented by the CCC value, example embodiments improve the reproducibility and reliability of tissue classification by systems, apparatus, processors, computers, and methods described herein compared to conventional approaches that do not consider feature stability.

Table 1 below illustrates an area under receiver operator characteristic curve (AUC) used to assess the predictive performance of different machine learning classifiers trained using radiomic features selected using one of three different feature selection approaches. In table 1, "KNN" refers to K nearest neighbors. "LDA" refers to linear discriminant analysis. "Poly" refers to a polynomial classifier. "QDA" refers to a quadratic discriminant analysis classifier. "RBF" refers to a radial basis function classifier. "RF" refers to a random forests classifier. "SVM" refers to a support vector machine.

TABLE 1

| AUC | KNN | LDA | Poly | QDA | RBF | RF | SVM |
| --- | --- | --- | --- | --- | --- | --- | --- |
| MRMR (6 top features) | 0.5 | 0.5 | 0.3769 | 0.5 | 0.5 | 0.5 | 0.7231 |
| T-test (4 top features) | 0.5 | 0.5385 | 0.4692 | 0.5923 | 0.5192 | 0.5 | 0.4692 |
| Wilcoxon (4 top features) | 0.5 | 0.5385 | 0.5077 | 0.5 | 0.5 | 0.5038 | 0.5846 |

FIG. 1 illustrates segmented tumor regions and heat maps of a Haralick (entropy) feature in a pre-treatment CT image and a post-treatment image of a responder. Segmented pre-treatment CT image 110 and segmented post-treatment CT image 112 are associated with a responder to immunotherapy. Enlargements of the segmented tumor regions are illustrated at 120 and 122 respectively. A heatmap 130 of a Haralick entropy feature for the pre-treatment CT image and a heatmap 132 of a Haralick entropy feature for the post-treatment CT image are illustrated. A legend 140 for the heatmaps 130 and 132 is also illustrated. Embodiments described herein may computer a difference between the pre-treatment Haralick entropy feature heatmap 130 and the post-treatment Haralick entropy feature heatmap 132.

Figure 2:
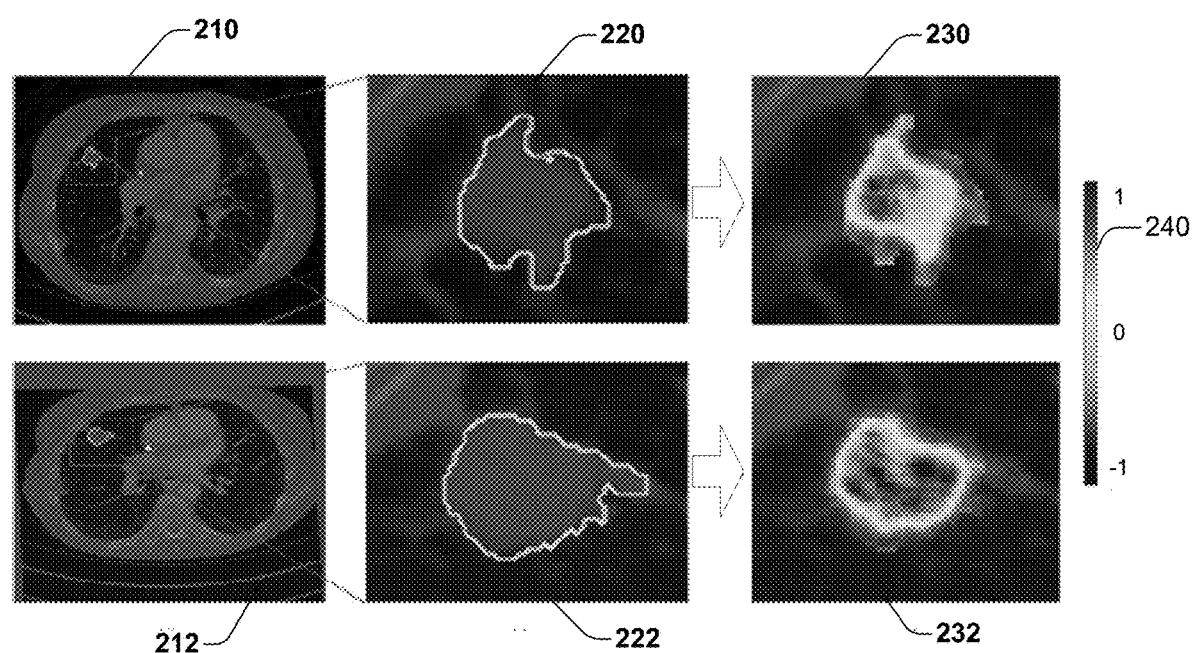
FIG. 2 illustrates segmented NSCLC tumor regions and a heatmap in pre-treatment and post-treatment CT images.

FIG. 2 illustrates segmented tumor regions and heat maps of a Haralick (entropy) feature in a pre-treatment CT image and a post-treatment image of a non-responder to immunotherapy. Segmented pre-treatment CT image 210 and segmented post-treatment CT image 212 are associated with the non-responder. Enlargements of the segmented tumor regions are illustrated at 220 and 222 respectively. A heatmap 230 of a Haralick entropy feature for the pre-treatment CT image and a heatmap 232 of a Haralick entropy feature for the post-treatment CT image are illustrated. A legend 240 for the heatmaps 230 and 232 is also illustrated. Embodiments described herein may computer a difference between the pre-treatment Haralick entropy feature heatmap 230 and the post-treatment Haralick entropy feature heatmap 232.

Figure 3:
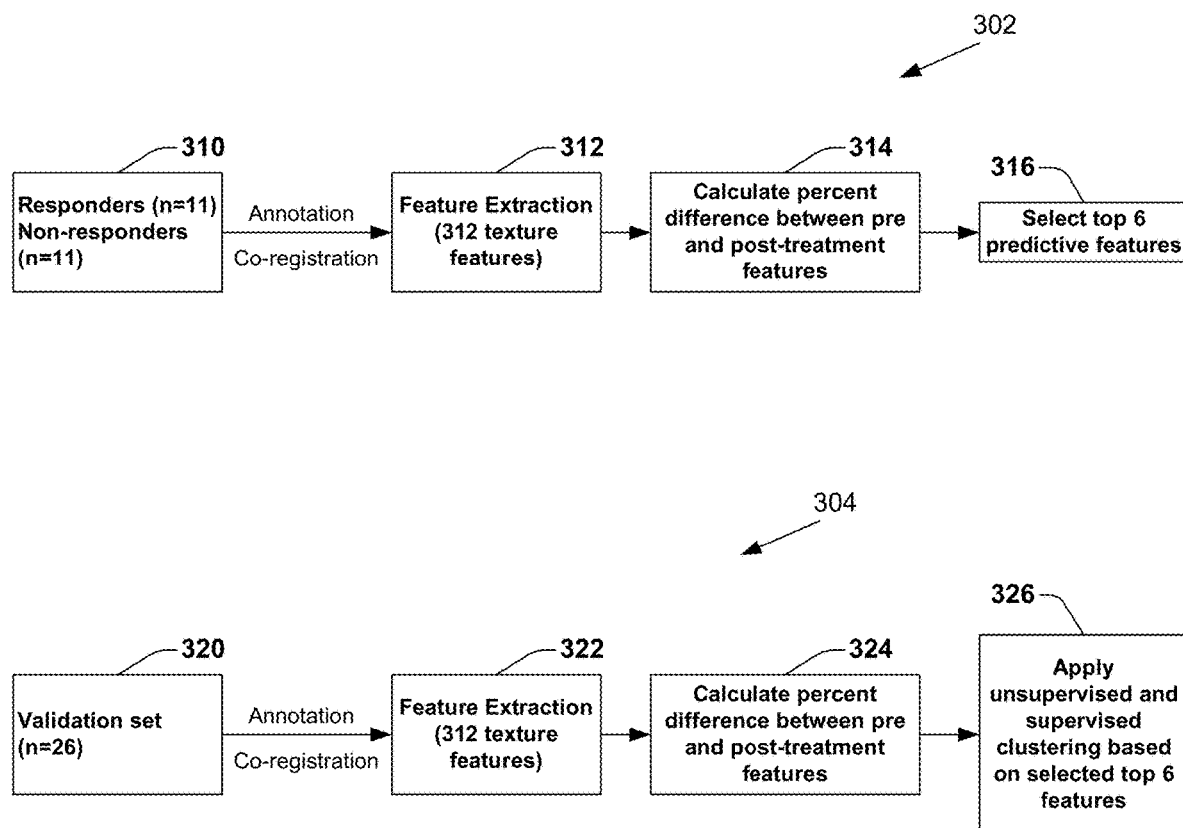
FIG. 3 is a schematic overview of a workflow to train and test a machine learning classifier to predict response to immunotherapy.

FIG. 3 is a schematic overview of a workflow to train and test a machine learning classifier suitable for use by embodiments described herein. FIG. 3 illustrates a first workflow 302 associated with a learning or training set of patients demonstrating NSCLC, and a second workflow 304 associated with a validation or testing set of patients demonstrating NSCLC that is disjoint from the training set. FIG. 3 illustrates, at 310, a training cohort of 22 patients including 11 responders and 11 non-responders. While 11 responders and 11 non-responders are illustrated in this example, other different numbers of responders and non-responders may be employed. The size of the training cohort may be determined based on available imagery, or may be based on an optimization of training effect or training time. Pre-treatment CT images and post-treatment CT images of a region of tissue demonstrating NSCLC are acquired of each member of the training cohort 310. A lung nodule or tumor represented in a pre-treatment CT image and in the corresponding post-treatment image is annotated, and the pre-treatment CT image is registered with the post-treatment CT image. In one embodiment, registered images may be normalized. At 312, a set of radiomic features is extracted from the registered images. In this example, texture features are extracted, while in another embodiment, intensity features, shape features or other radiomic features may be extracted. At 314, a percent difference is computed between features extracted from the pre-treatment and corresponding post-treatment images to generate a set of delta-radiomic features. At 316, the top 6 features predictive of response to immunotherapy are selected. While the top 6 features are selected in this example, other different numbers of features may be selected.

FIG. 3 further illustrates a testing or validation cohort 320 of 26 patients demonstrating NSCLC. Pre-treatment CT images and post-treatment CT images of a region of tissue demonstrating NSCLC are acquired from members of the validation cohort 320. A lung nodule or tumor represented in a pre-treatment CT image and in the corresponding post-treatment CT image is annotated, and the pre-treatment CT image is registered with the post-treatment CT image. At 322, a set of radiomic features is extracted from the registered images. In this example, texture features are extracted, while in another embodiment, shape features, intensity features, or other radiomic features may be extracted. At 324, a percent difference is computed between features extracted from the pre-treatment and corresponding post-treatment images to generate a set of delta radiomic features. While in this example a percent difference is computed, in other embodiments, other measures of difference may be employed to generate the set of delta radiomic features. The set of delta-radiomic features selected is based on the top 6 features selected at 316. At 326, unsupervised and supervised clustering is applied based on the set of delta-radiomic features, to characterize the patient as a responder or non-responder.

Example methods and apparatus demonstrably improve on conventional technologies for predicting response to immunotherapy. For example, embodiments described herein predict response to nivolumab immunotherapy with an average area under the curve (AUC) accuracy of at least 0.72, compared with conventional approaches such as overexpression of the PDL1 biomarker which has an accuracy of only approximately 50%. By increasing the accuracy with which response to immunotherapy is predicted, example methods and apparatus produce the concrete, real-world technical effect of increasing the probability that at-risk patients receive timely treatment tailored to the particular pathology they exhibit. The additional technical effect of reducing the expenditure of resources and time on patients who have a less aggressive pathology is also achieved. Example embodiments further improve on conventional approaches by providing a more accurate second reader to facilitate the reduction of inter-reader variability among human radiologists or oncologists. Example methods and apparatus thus improve on conventional methods in a measurable, clinically significant way.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 4:
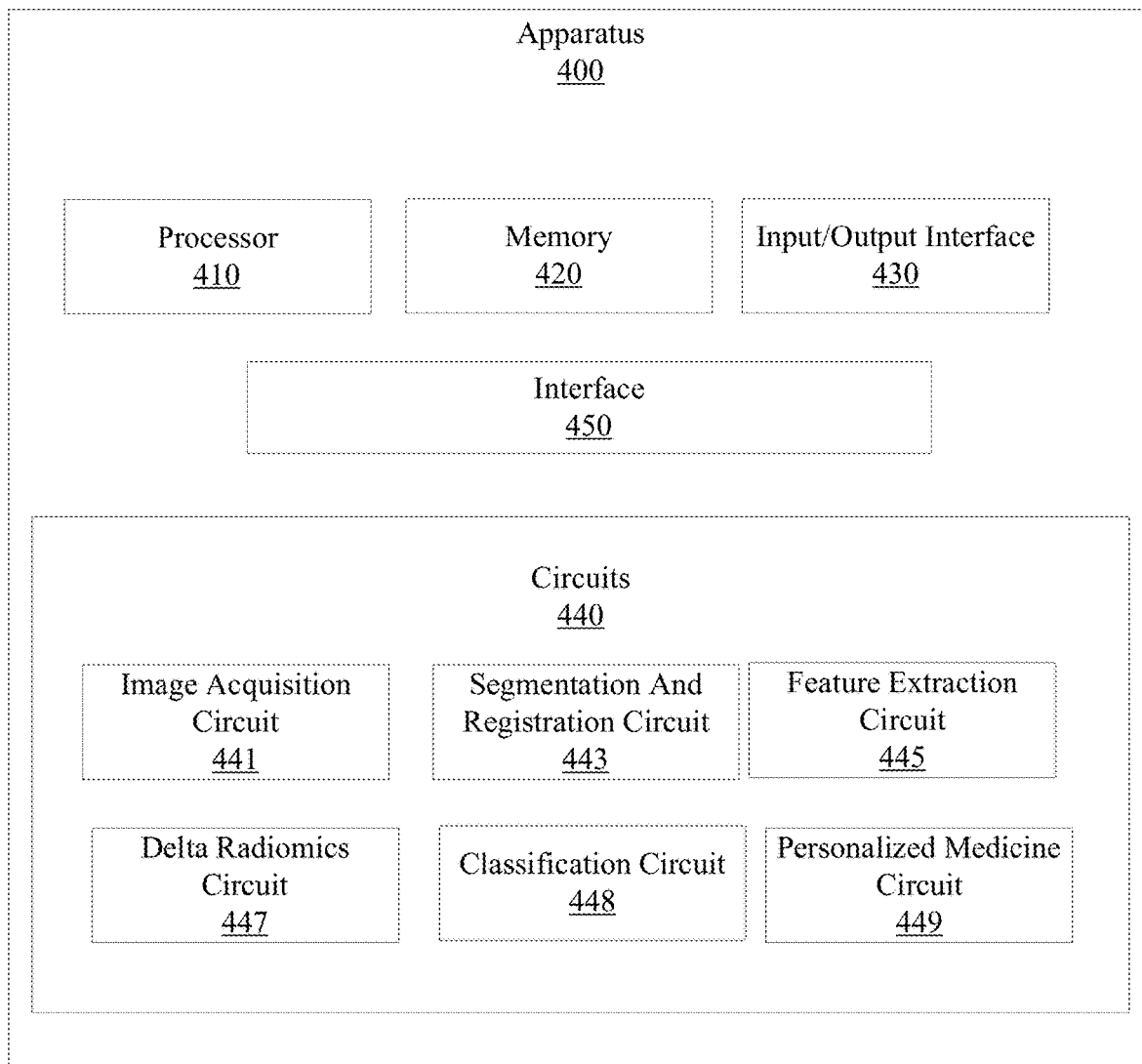
FIG. 4 illustrates an example apparatus that predicts response to immunotherapy.

FIG. 4 illustrates an example apparatus 400 that predicts patient response to immunotherapy. Apparatus 400 includes a processor 410, a memory 420, an input/output interface 430, a set of circuits 440, and an interface 450 that connects the processor 410, the memory 420, the input/output interface 430, and the set of circuits 440. The set of circuits 440 includes an image acquisition circuit 441, a segmentation and registration circuit 443, a feature extraction circuit 445, a delta radiomics circuit 447, a classification circuit 448, and a personalized medicine circuit 449.

Memory 420 is configured to store a digitized CT pre-treatment image and at least one digitized CT post-treatment image of a region of tissue demonstrating NSCLC. At least one CT pre-treatment image and a member of the at least one CT post-treatment image are of the same patient. The at least one CT post-treatment image is acquired at least a threshold time after the CT pre-treatment image. In one embodiment, the at least one CT post-treatment image is acquired two weeks after the administration of immunotherapy treatment to the patient. In another embodiment, the at least one CT post-treatment image may be acquired at a different time interval after the administration of immunotherapy. The region of tissue includes a tumor or nodule. The pre-treatment image has a plurality of voxels and the at least one post-treatment image has a plurality of voxels. A voxel has an intensity value. In other embodiments, a pre-treatment image and at least one post-treatment image may be radiological images acquired using other imaging systems, or be of other regions demonstrating other types of pathology.

Image acquisition circuit 441 is configured to access the pre-treatment image and the at least one post-treatment image. Accessing the pre-treatment image and the at least one post-treatment image includes acquiring electronic data, reading from a computer file, receiving a computer file, reading from a computer memory, or other computerized activity. Accessing the pre-treatment image and the at least one post-treatment image may include accessing a digitized CT pre-treatment image and at least one digitized CT post-treatment image of a region of tissue demonstrating NSCLC stored in memory 420. In another embodiment, accessing the pre-treatment image and the at least one post-treatment image may include accessing a network attached storage (NAS), a cloud storage system, or other type of electronic storage system. Accessing the pre-treatment image and the at least one post-treatment image may, in one embodiment, include accessing a network attached storage (NAS), a cloud storage system, or other type of electronic storage system using input/output interface 430.

Segmentation and registration circuit 443 is configured to annotate the tumor represented in the pre-treatment image. Segmentation and registration circuit 443 is further configured to annotate the tumor represented in the at least one post-treatment image. In one embodiment, segmentation and registration circuit 443 is configured to annotate the tumor using 3D Slicer software, or using an automated segmentation approach. An automated segmentation approach may include, for example, an ensemble segmentation approach, a level set model, or a combined spectral embedding/active contour (SEAC) approach.

Segmentation and registration circuit 443 is further configured to generate a registered image by registering the pre-treatment image with the at least one post-treatment image. Segmentation and registration circuit 443 may register the pre-treatment image, after the tumor is annotated in the pre-treatment image and after the tumor is annotated in the at least one post-treatment image, with the at least one post-treatment image. In one embodiment, segmentation and registration circuit 443 registers the pre-treatment image with the at least one post-treatment image using an affine registration approach based, at least in part, on the annotated tumors represented in the pre-treatment image and the at least one post-treatment image. In another embodiment, segmentation and registration circuit 443 registers the pre-treatment image with the at least one post-treatment image using a rigid registration approach or a deformable registration approach. In another embodiment, other registration techniques may be employed.

Feature extraction circuit 445 is configured to select a set of pre-treatment radiomic features from the registered image and to select a set of post-treatment radiomic features from the registered image. In one embodiment, feature extraction circuit 445 selects the set of pre-treatment radiomic features and the set of post-treatment radiomic features based on a threshold level of reliability and a threshold level of reproducibility associated with the radiomic features. The reliability and reproducibility may be expressed as a level of stability between a pre-treatment radiomic feature and its post-treatment counterpart. For example, feature extraction circuit 445 may compute a level of stability between a Haralick (entropy) feature extracted from the pre-treatment image and the same Haralick (entropy) feature extracted from the associated post-treatment image acquired of the same patient. The feature extraction circuit 445 computes the threshold level of reliability and the threshold level of reproducibility using a concordance correlation coefficient (CCC) approach. In one embodiment, a CCC value of 0.8 is used as a threshold level of stability. In another embodiment, other, different CCC values may be employed. In another embodiment, other approaches to computing a level of stability may be employed.

In one embodiment, the set of pre-treatment radiomic features includes a Sobel y gradient feature, a Laws gradient x feature, a Laws E3L3E3 feature, a Sobel yz gradient feature, a Laws L3S3E3 feature, and a Laws E5S5L5 feature. In this embodiment, the set of post-treatment radiomic features includes a Sobel y gradient feature, a Laws gradient x feature, a Laws E3L3E3 feature, a Sobel yz gradient feature, a Laws L3S3E3 feature, and a Laws E5S5L5 feature. In another embodiment, other radiomic features may be selected, including other texture features, shape features, intensity features, or other, different radiomic features. While in this embodiment six radiomic features are selected, in another embodiment, other, different numbers of radiomic features may be selected.

In one embodiment, feature extraction circuit 445 is further configured to normalize the set of pre-treatment radiomic features and the set of post-treatment radiomic features. Normalizing the set of pre-treatment radiomic features and the set of post-treatment radiomic features may include normalizing feature intensity values to a notionally common scale between −1 and 1.

Delta radiomics circuit 447 is configured to generate a set of delta radiomic features based on the set of pre-treatment radiomic features and the set of post-treatment radiomic features. Delta radiomics circuit 447 generates the set of delta radiomic features by computing a difference between the set of post-treatment radiomic features and the set of pre-treatment radiomic features. Delta radiomics circuit 447 generates the set of delta radiomic features on a per-voxel basis. In one embodiment, a value for a member of the set of delta radiomic features may be computed as a percent difference PD $$\text{as} := \frac{\text{pre-post}}{\text{pre}} * 100,$$

where pre is a value for a pre-treatment radiomic feature and post is a value for the corresponding post-treatment radiomic feature. In one embodiment, the pre and post values represent the statistical measurement for the radiomic feature expression calculated over the surface or volume of the nodule. For example, the difference may be a difference in the statistical mean or standard deviation of the radiomic feature value over the nodule. In another embodiment, delta radiomics circuit 447 may compute a difference between the set of post-treatment radiomic features and the set of pre-treatment radiomic features using another, different technique.

Delta radiomics circuit 447 is further configured to provide the set of delta radiomic features to the classification circuit 448. Providing the set of delta radiomics features to the classification circuit 448 includes acquiring electronic data, reading from a computer file, receiving a computer file, reading from a computer memory, or other computerized activity.

Classification circuit 448 is configured to generate a probability that the region of tissue will respond to immunotherapy. Classification circuit 448 computes the probability based, at least in part, on the set of delta radiomic features. Classification circuit 448 is further configured to classify the region of tissue as a responder or non-responder based, at least in part, on the probability. In one embodiment, classification circuit 448 includes a machine learning classifier. The machine learning classifier may be a support vector machine (SVM) classifier. In one embodiment, the SVM has three kernels, including a linear kernel, a radial basis function (RBF) kernel, and a polynomial kernel. In another embodiment, the machine learning classifier is a discriminant analysis (DA) classifier, a nearest neighbor (NN) classifier, a convolutional neural network (CNN), or a random forest (RF) classifier. In this embodiment, apparatus 400 classifies a region of tissue as a responder or non-responder with an AUC of at least 0.72.

Classification circuit 448 resolves features extracted from the digitized CT imagery at a higher order or higher level than a human can resolve in the human mind or with pencil and paper. For example, the intensity values for a voxel in a digitized CT image are not biological properties of physical lung tissue that a human eye can perceive. The radiomic features, including texture features, shape features, and other radiomic features, are of a different nature than the intensity values or the physical properties of the biological tissue represented in the CT imagery. A section of lung tissue in a patient does not comprise, for example, a Sobel y gradient feature, a Laws gradient x feature, or a Laws E3L3E3 feature. The probability computed by classification circuit 448 is of a different nature than the radiomic features.

Personalized medicine circuit 449 is configured to generate an NSCLC immunotherapy treatment for the patient represented in the pre-treatment and post-treatment image. Personalized medicine circuit 449 generates the plan based, at least in part, on the classification and at least one of the probability, the set of delta radiomic features, the pre-treatment image, or the at least one post-treatment image. The NSCLC immunotherapy treatment plan defines an immunotherapy drug dosage amount and an immunotherapy drug dosage schedule. Defining a personalized NSCLC immunotherapy treatment plan facilitates delivering a particular treatment that will be therapeutically active to the patient, while minimizing negative or adverse effects experienced by the patient. For example, the NSCLC immunotherapy treatment plan may define a nivolumab dosage amount and schedule for a patient identified as a responder, while for a non-responder, other treatments may be suggested. In one embodiment, personalized medicine circuit 449 may control an immunotherapy dosage system to administer a dosage of an immunotherapy agent defined by the NSCLC immunotherapy plan by an intravenous infusion, or by an intravesical infusion.

In another embodiment, personalized medicine circuit 449 may control a computer aided diagnosis (CADx) system to classify the region of tissue represented in the pre-treatment and post-treatment imagery, based, at least in part, on the probability or the classification generated by classification circuit 448. For example, personalized medicine circuit 449 may control a CADx system to predict response to immunotherapy based, at least in part, on the probability or the classification generated by classification circuit 449.

In other embodiments, other types of CADx systems may be controlled, including CADx systems for predicting patient response to other types of immunotherapy or to predict response to immunotherapy in other tissue presenting other, different pathologies that may be distinguished based on features extracted by feature extraction circuit 445 and computed by delta radiomics circuit 447 that are represented in serial CT imagery or other type of radiological image. For example, embodiments described herein may be employed to predict response to immunotherapy based on probabilities computed from delta radiomics by a machine learning classifier in breast cancer (BCa), kidney disease, or brain pathologies.

Figure 5:
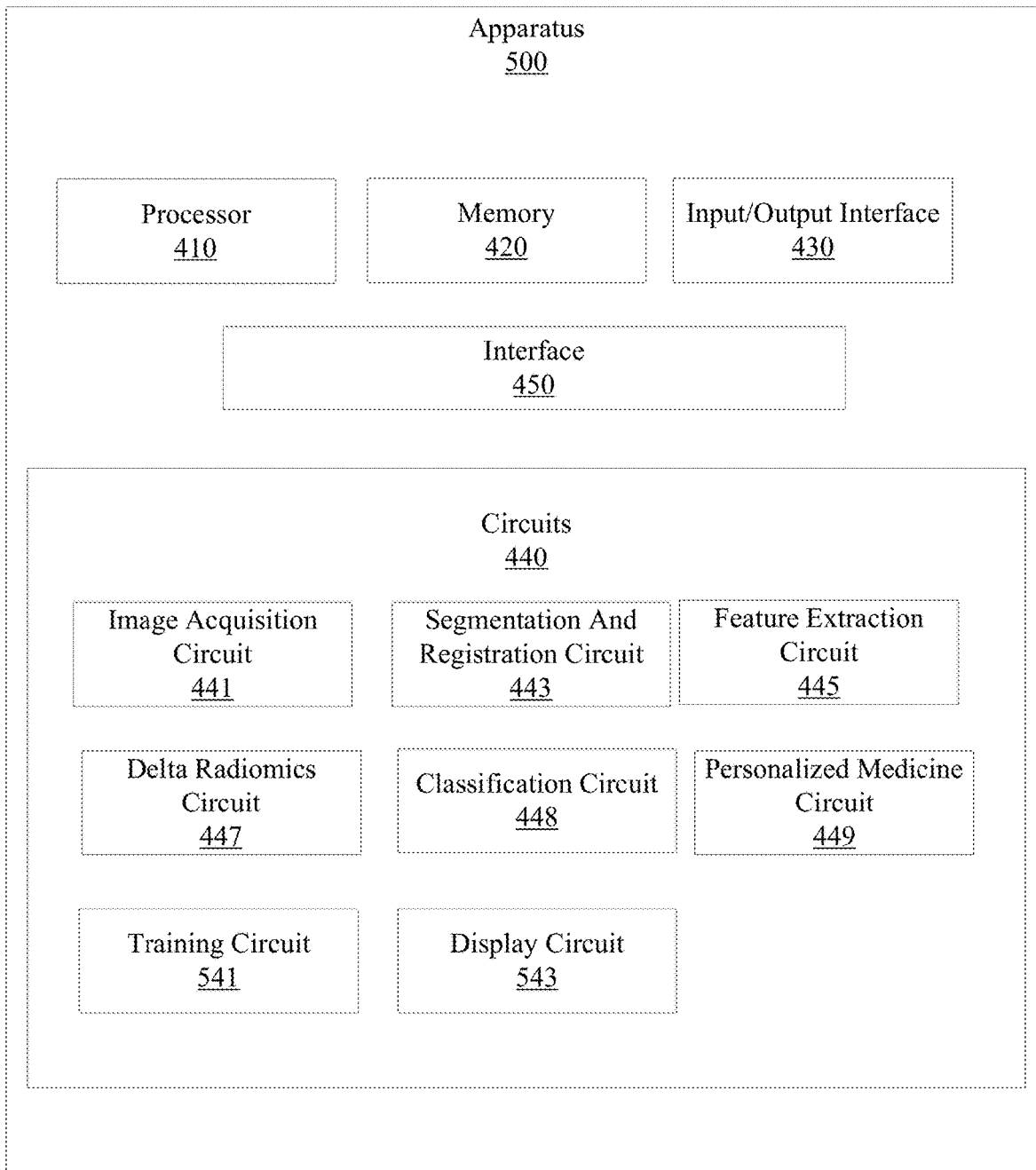
FIG. 5 illustrates an example apparatus that predicts response to immunotherapy.

FIG. 5 illustrates an apparatus 500 that is similar to apparatus 400 but that includes additional elements and details. In one embodiment of apparatus 500, the set of circuits 440 further includes a training circuit 541 configured to train classification circuit 448. Training classification circuit 448 may include training the machine learning classifier. In one embodiment, the training circuit 541 accesses a dataset of CT images of a region of tissue demonstrating NSCLC. A first member of the dataset is a pre-treatment image, and a second member of the dataset is a post-treatment image of the region represented in the first member. The post-treatment image is acquired at least a threshold period of time (e.g. two weeks) after the administration of immunotherapy to the patient represented in the pre-treatment image and the post-treatment image. Training circuit 541 selects a set of training delta radiomic features from the dataset. The set of training delta radiomic images includes a feature selected from the first member, and a corresponding feature selected from the associated second member. The set of training delta radiomic features is selected based on a level of discriminability and on a level of stability. In one embodiment, the level of stability is computed using a concordance correlation coefficient (CCC) approach. Radiomic features that do not meet the level of stability are not selected. Training circuit 541 trains the classification circuit 448 using the set of delta radiomic features. Training circuit 541 may employ supervised or unsupervised learning to train classification circuit 448. Training circuit 541 may train the classification circuit 448 until a desired level of accuracy is achieved by classification circuit 448, until a threshold period time has been used to train classification circuit 448, until a threshold level of computational resources have be expended, until a signal instructing training circuit 541 to terminate training is received by training circuit 541, or until some other, different condition has been met.

In one embodiment of apparatus 500, the set of circuits 440 further includes a display circuit 543. The display circuit may control the personalized medicine circuit 449 or a CADx system to display the classification, the probability, the pre-treatment image, the post-treatment image, the NSCLC immunotherapy treatment plan, or the set of delta radiomic features on a computer monitor, a smartphone display, a tablet display, or other displays. Displaying the classification, the probability, the pre-treatment image, the post-treatment image, the NSCLC immunotherapy treatment plan, or the set of delta radiomic features may also include printing the classification, the probability, the pre-treatment image, the post-treatment image, or the set of delta radiomic features. The display circuit may also control the personalized medicine circuit 449, the classification circuit 448, or the CADx system to display operating parameters or characteristics of the machine learning classifier, during both training and testing, and clinical operation. Displaying the classification, the probability, the pre-treatment image, the post-treatment image, the NSCLC immunotherapy treatment plan, or the set of delta radiomics involves but is not limited to extracting and changing the character of information present in a region of tissue (e.g. biological tissue), to a radiological image (e.g. CT image), to changing the information present in the radiological image to information of a different character in the radiomic features, the probability, the characterization, and the NSCLC immunotherapy treatment plan. Embodiments described herein further transform the character of information to information suitable for display on, for example, a computer monitor, a smartphone display, a tablet display, or other displays. Thus, embodiments described herein use a combined order of specific rules that render information into a specific format that is then used and applied to create desired results more accurately and with greater reliability than conventional approaches: a prediction of response to immunotherapy based on a difference computed from the set of delta radiomic features.

Figure 6:
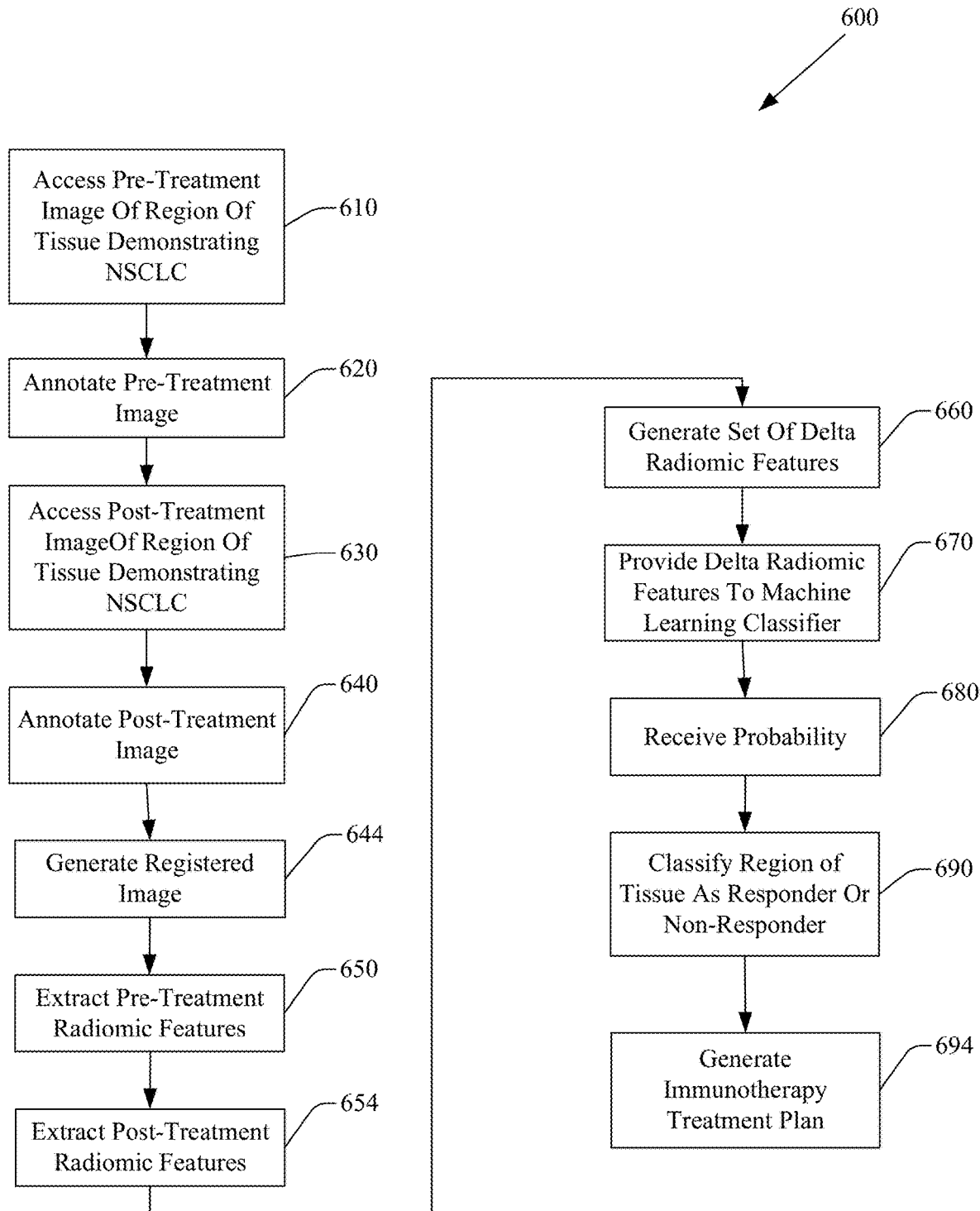
FIG. 6 illustrates an example method for predicting response to immunotherapy.

FIG. 6 illustrates a computerized method 600 for predicting NSCLC patient response to immunotherapy. Method 600 includes, at 610, accessing a pre-treatment image of a region of tissue demonstrating NSCLC. The pre-treatment image includes a representation of a tumor. The pre-treatment image includes a plurality of voxels. A voxel has an intensity value. In one embodiment, the pre-treatment image is a computed tomography (CT) image of a first patient. Accessing a pre-treatment image of a region of tissue demonstrating NSCLC includes acquiring electronic data, reading from a computer file, receiving a computer file, reading from a computer memory, or other computerized activity. In other embodiments, other, different types of tissue demonstrating other, different pathologies may be imaged using different imaging techniques.

Method 600 also includes, at 620, annotating the tumor represented in the pre-treatment image. Annotating the tumor represented in the pre-treatment image includes segmenting the tumor from other, non-tumor regions represented in the image.

Method 600 also includes, at 630, accessing at least one post-treatment image of the region of tissue demonstrating NSCLC. The at least one post-treatment image includes the tumor represented in the pre-treatment image. The at least one post-treatment image is acquired of the patient at least a first time interval after the pre-treatment image. In one embodiment, the first time interval is two weeks. The post-treatment image includes a plurality of voxels. A voxel has an intensity value. In one embodiment, the at least one post-treatment image is a CT image of the region of tissue represented in the pre-treatment image of the first patient. Accessing a post-treatment image of the region of tissue demonstrating NSCLC includes acquiring electronic data, reading from a computer file, receiving a computer file, reading from a computer memory, or other computerized activity. In other embodiments, different types of tissue demonstrating other, different pathologies may be imaged using different imaging techniques. For example, in another embodiment, the pre-treatment image and the post-treatment image may be MRI images, combined CT/PET images, or other radiological images of NSCLC tissue or other tissue demonstrating cancerous pathology.

Method 600 also includes, at 640, annotating the tumor represented in the at least one post-treatment image. Annotating the tumor represented in the pre-treatment image or the at least one post-treatment image includes segmenting a tumor or nodule region from the background of the image. The tumor represented in the pre-treatment image or the at least one post-treatment image may be annotated using 3D Slicer software, or may be automatically segmented. Automatically segmenting the tumor may include, for example, controlling a computer or processor to use an ensemble segmentation approach, a level set model, or a combined spectral embedding/active contour (SEAC) approach to segment the tumor.

Method 600 also includes, at 644, generating a registered image by registering the pre-treatment image with the at least one post-treatment image. In one embodiment, registering the pre-treatment image with the at least one post-treatment image includes registering the pre-treatment image with the at least one post-treatment image using an affine registration approach. In another embodiment, the pre-treatment image may be registered with the at least one post-treatment image using a rigid registration approach, or a deformable registration approach.

Method 600 also includes, at 650 extracting a set of pre-treatment radiomic features from the registered image. Method 600 also includes, at 654, extracting a set of post-treatment radiomic features from the registered image. In one embodiment, the set of pre-treatment radiomic features and the set of post-treatment radiomic features are selected using a T-test score approach, a Wilcoxon rank sum approach, or a minimum redundancy maximum relevancy (mRMR) approach.

In one embodiment, method 600 further includes normalizing the set of pre-treatment radiomic features and the set of post-treatment radiomic features. Normalizing the set of pre-treatment radiomic features and the set of post-treatment radiomic features may include normalizing feature intensity values to a notionally common scale between −1 and 1. In another embodiment, other normalization techniques may be employed.

The set of pre-treatment radiomic features includes a Sobel y gradient feature, a Laws gradient x feature, a Laws E3L3E3 feature, a Sobel yz gradient feature, a Laws L3S3E3 feature, and a Laws E5S5L5 feature. The set of post-treatment radiomic features includes a Sobel y gradient feature, a Laws gradient x feature, a Laws E3L3E3 feature, a Sobel yz gradient feature, a Laws L3S3E3 feature, and a Laws E5S5L5 feature. In another embodiment, other, different radiomic features may be selected. For example, other, different texture features, intensity features, or shape features may be extracted from the registered image. While six radiomic features are extracted in this embodiment, in another embodiment, other, different numbers of radiomic features may be extracted.

Method 600 also includes, at 660, generating a set of delta radiomic features. Generating the set of delta radiomic features includes computing, on a per-voxel basis, a difference between the set post-treatment radiomic features and the set of pre-treatment radiomic features. In another embodiment, delta-radiomic features may be generated by computing, for a threshold number of voxels, a difference between the set post-treatment radiomic features and the set of pre-treatment radiomic features. The set of delta radiomic features may be selected using a concordance correlation coefficient (CCC) approach. In one embodiment, a CCC value of 0.8 is used as a threshold level of stability. In this embodiment, delta radiomic features with a CCC value of 0.8 or greater are selected. In another embodiment, other different CCC values may be employed. Different CCC values may result in different levels of stability for the set of delta radiomic features. The CCC value may be user-selected, or may be defined as a function of a desired level of stability or accuracy in predicting response to NSCLC.

Method 600 also includes, at 670, providing the set of delta radiomic features to a machine learning classifier. In one embodiment, the machine learning classifier is a support vector machine (SVM) classifier. In one embodiment, the SVM classifier has three kernels, including a linear kernel, a radial basis function (RBF) kernel, and a polynomial kernel. In another embodiment, the machine learning classifier is a discriminant analysis (DA) classifier, a nearest neighbor (NN) classifier, a convolutional neural network, or a random forest (RF) classifier. Providing the set of delta radiomic features to the machine learning classifier may include acquiring electronic data, reading from a computer file, receiving a computer file, reading from a computer memory, or other computerized activity.

Method 600 also includes, at 680, receiving, from the machine learning classifier, a probability that the region of tissue will respond to immunotherapy. The probability is based, at least in part, on the set of delta radiomic features. Receiving the probability from the machine learning classifier may include acquiring electronic data, reading from a computer file, receiving a computer file, reading from a computer memory, or other computerized activity.

Method 600 also includes at 690, classifying the region of tissue as a responder or non-responder based, at least in part, on the probability. In one embodiment, classifying the region of tissue as a responder or non-responder may include classifying the region as a responder when the machine learning classifier provides a probability of 0.5 or greater. In another embodiment, classifying the region of tissue as a responder may be based on other probability values. In another embodiment, classifying the region of tissue may include categorizing the region of tissue based on more than two categories. For example, the region of tissue may be classified as one of "least likely to respond", "neutral", or "most likely to respond" based on the probability. Other categorization schemes may be employed.

Method 600 further includes, at 694, controlling a personalized medicine system to generate an NSCLC immunotherapy treatment plan for the patient from which the pre-treatment image and the post-treatment image were acquired. The NSCLC immunotherapy treatment plan is based, at least in part, on the classification and at least one of the probability, the set of delta radiomic features, the pre-treatment image, or the at least one post-treatment image. In one embodiment, the NSCLC immunotherapy treatment plan defines an immunotherapy drug or agent dosage amount or an immunotherapy drug or agent dosage schedule. In one embodiment, method 600 further includes controlling an immunotherapy dosage system to administer a dosage of an immunotherapy agent defined by the NSCLC immunotherapy plan by intravenous infusion, by intravesical infusion, or through another, different technique.

Improved identification or classification of patients who will respond to immunotherapy may produce the technical effect of improving treatment efficacy by increasing the accuracy of and decreasing the time required to treat patients demonstrating NSCLC or other forms of cancerous pathology. Treatments and resources, including expensive immunotherapy agents, may be more accurately tailored to patients with a likelihood of benefiting from said treatments and resources, including responding to immunotherapy, so that more appropriate treatment protocols may be employed, and expensive resources are not wasted. Controlling an immunotherapy dosage system based on improved identification or classification of patients who will respond to immunotherapy further improves the operation of the immunotherapy dosage system, since unnecessary operations will not be performed.

Using a more appropriately modulated treatment may lead to less aggressive therapeutics being required for a patient or may lead to avoiding or delaying a biopsy, a resection, or other invasive procedure. When patients experiencing NSCLC who will respond to immunotherapy are more quickly and more accurately distinguished from patients who will not, patients most at risk may receive a higher proportion of scarce resources (e.g., therapeutics, physician time and attention, hospital beds) while those less likely to benefit from the treatment may be spared unnecessary treatment, which in turn spares unnecessary expenditures and resource consumption. Example methods, apparatus, and other embodiments may thus have the additional effect of improving patient outcomes compared to conventional approaches.

While FIG. 6 illustrates various actions occurring in serial, it is to be appreciated that various actions illustrated in FIG. 6 could occur substantially in parallel. By way of illustration, a first process could involve extracting radiomic features from a pre-treatment CT image, a second process could involve extracting radiomic features from a post-treatment CT image, and a third process could involve registering the pre-treatment CT image with the post-treatment CT image. While three processes are described, it is to be appreciated that a greater or lesser number of processes could be employed and that lightweight processes, regular processes, threads, and other approaches could be employed.

In one example, a method may be implemented as computer executable instructions. Thus, in one example, a computer-readable storage medium may store computer executable instructions that if executed by a machine (e.g., computer, processor) cause the machine to perform methods described or claimed herein including method 600 and method 700. While executable instructions associated with the listed methods are described as being stored on a computer-readable storage medium, it is to be appreciated that executable instructions associated with other example methods described or claimed herein may also be stored on a computer-readable storage medium. In different embodiments the example methods described herein may be triggered in different ways. In one embodiment, a method may be triggered manually by a user. In another example, a method may be triggered automatically.

Figure 7:
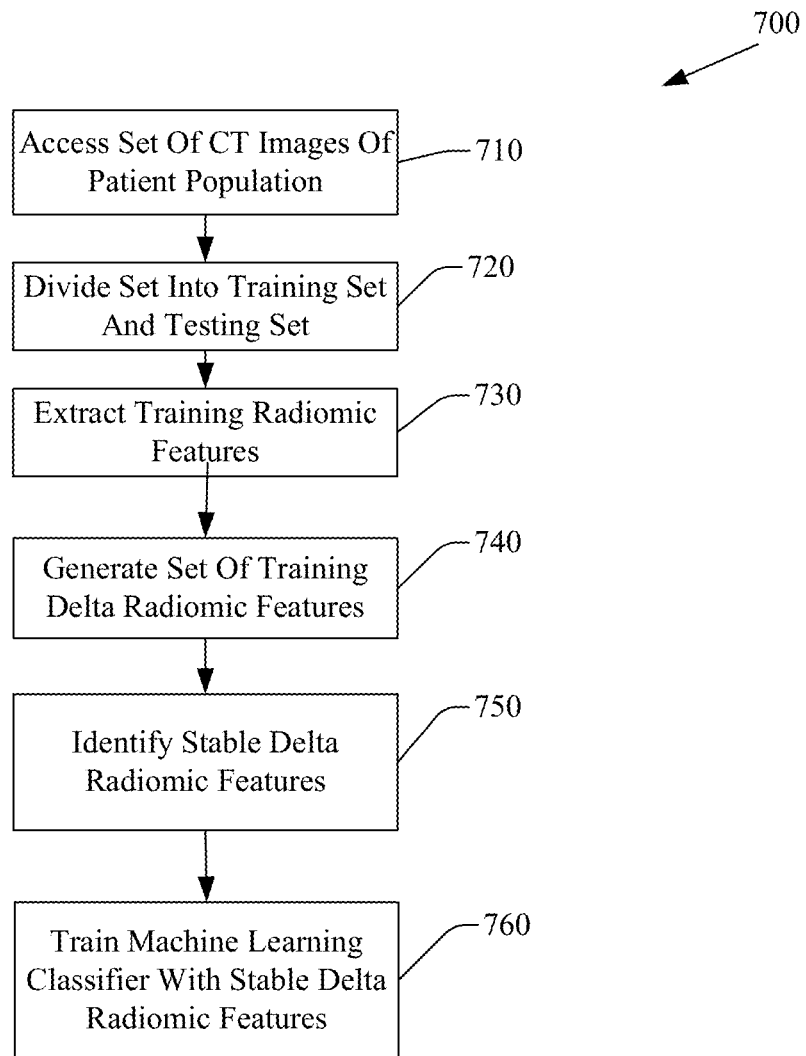
FIG. 7 illustrates an example method for training a machine learning classifier to predict response to immunotherapy.

In one embodiment, method 600 further includes training the machine learning classifier. FIG. 7 illustrates an example method 700 for training a machine learning classifier to predict patient response to immunotherapy. Method 700 includes, at 710, accessing a set of CT images of a population of NSCLC patients. The population of NSCLC patients includes a set of responders and a set of non-responders. A member of the set of CT images includes a representation of a tumor or nodule in the region of tissue represented in the member of the set of CT images. The tumor or nodule may be annotated. A member of the set of CT images includes a voxel. A voxel has an intensity. The set of CT images includes at least one pre-treatment image associated with a responder member of the population and at least one post-treatment image associated with the responder member. The set of CT images also includes at least one pre-treatment image associated with a non-responder member of the population and at least one post-treatment image associated with the non-responder member.

Method 700 also includes, at 720, dividing the set of CT images into a training set and a testing set. The training set includes at least one pre-treatment CT image and at least one post-treatment CT image associated with a responder, and at least one pre-treatment CT image and at least one post-treatment CT image associated with a non-responder. The testing set includes at least one pre-treatment CT image and at least one post-treatment CT image associated with a responder, and at least one pre-treatment CT image and at least one post-treatment CT image associated with a non-responder.

Method 700 also includes, at 730, extracting a set of training pre-treatment radiomic features and a set of training post-treatment radiomic features from the training set. The set of training pre-treatment radiomic features and the set of training post-treatment radiomic features may be extracted from the annotated tumor represented in a member of the training set. In one embodiment, the set of training pre-treatment radiomic features includes a Sobel y gradient feature, a Laws gradient x feature, a Laws E3L3E3 feature, a Sobel yz gradient feature, a Laws L3S3E3 feature, and a Laws E5S5L5 feature. The set of training post-treatment radiomic features includes a Sobel y gradient feature, a Laws gradient x feature, a Laws E3L3E3 feature, a Sobel yz gradient feature, a Laws L3S3E3 feature, and a Laws E5S5L5 feature. In another embodiment, other, different radiomic features may be selected. For example, other, different texture features, intensity features, or shape features may be extracted from the registered image. While six radiomic features are extracted for training in this embodiment, in another embodiment, other, different numbers of radiomic features may be extracted. In one embodiment, the set of training pre-treatment radiomic features and the set of training post-treatment radiomic features are selected using a T-test score approach, a Wilcoxon rank sum approach, or a minimum redundancy maximum relevancy (mRMR) approach.

Method 700 also includes, at 740, generating a set of training delta radiomic features. The set of training delta radiomic features may be generated by computing, on a per-voxel basis, a difference between the set of training post-treatment radiomic features and the set of training pre-treatment radiomic features. In another embodiment, the set of training delta radiomic features may be generated by computing, for a threshold level of voxels (e.g., one half or one quarter of the voxels in an image), a difference between the set of training post-treatment radiomic features and the set of training pre-treatment radiomic features. In one embodiment, the difference may be a difference in the statistical mean or standard deviation of a radiomic feature value over the nodule or tumor.

Method 700 also includes, at 750, identifying a set of stable delta radiomic features in the set of training delta radiomic features. In one embodiment, the set of stable delta radiomic features are selected based on a threshold level of reliability and a threshold level of reproducibility. The set of stable delta radiomic features may be selected using a concordance correlation coefficient (CCC) approach. In one embodiment, a CCC value of 0.8 is used as a threshold level of stability. In this embodiment, delta radiomic features with a CCC value of 0.8 or greater are selected. In another embodiment, other different CCC values may be employed. Other approaches to identifying the set of stable delta radiomic features may be employed.

Method 700 further includes, at 760, training the machine learning classifier using the set of stable delta radiomic features. In one embodiment, the machine learning classifier may be trained using supervised learning. In another embodiment, other machine learning techniques may be employed. In one embodiment, method 700 further includes testing the machine learning classifier using the testing set.

Figure 8:
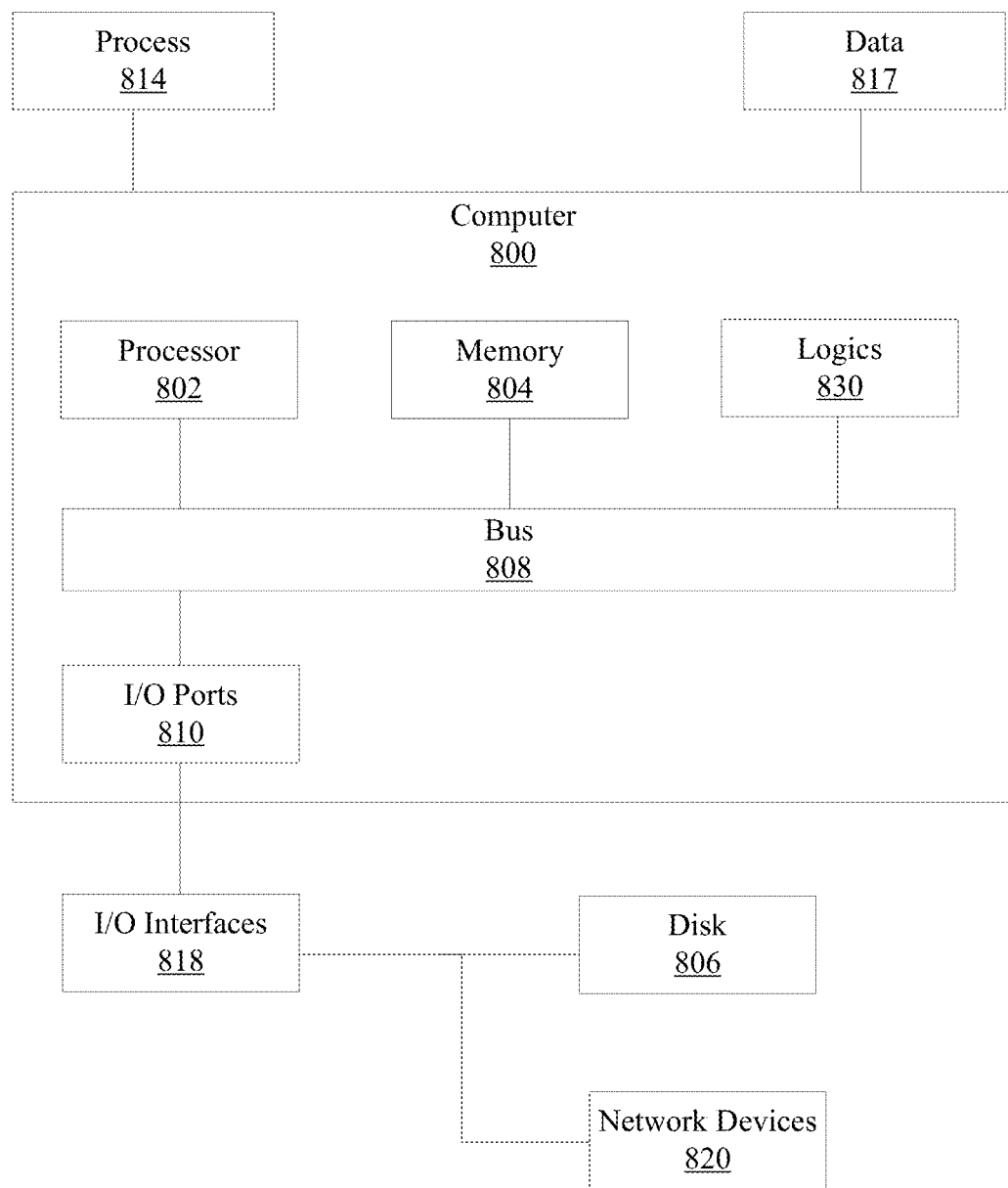
FIG. 8 illustrates an example computer in which example embodiments described herein may operate.

FIG. 8 illustrates an example computer 800 in which example methods illustrated herein can operate and in which example methods, apparatus, circuits or logics may be implemented. In different examples, computer 800 may be part of a personalized medicine system, may be operably connectable to a CT system, a personalized medicine system, or may be part of a CADx system.

Computer 800 includes a processor 802, a memory 804, and input/output (I/O) ports 810 operably connected by a bus 808. In one example, computer 800 may include a set of logics or circuits 830 that perform a method of predicting NSCLC patient response to immunotherapy using a machine learning classifier. Thus, the set of circuits 830, whether implemented in computer 800 as hardware, firmware, software, and/or a combination thereof may provide means (e.g., hardware, firmware, circuits) for predicting patient response to immunotherapy, and a machine learning classifier. In different examples, the set of circuits 830 may be permanently and/or removably attached to computer 800.

Processor 802 can be a variety of various processors including dual microprocessor and other multi-processor architectures. Processor 802 may be configured to perform steps of methods claimed and described herein. Memory 804 can include volatile memory and/or non-volatile memory. A disk 806 may be operably connected to computer 800 via, for example, an input/output interface (e.g., card, device) 818 and an input/output port 810. Disk 806 may include, but is not limited to, devices like a magnetic disk drive, a tape drive, a Zip drive, a flash memory card, or a memory stick. Furthermore, disk 806 may include optical drives like a CD-ROM or a digital video ROM drive (DVD ROM). Memory 804 can store processes 814 or data 817, for example. Data 817 may, in one embodiment, include digitized CT images of a region of tissue demonstrating NSCLC. Disk 806 or memory 804 can store an operating system that controls and allocates resources of computer 800.

Bus 808 can be a single internal bus interconnect architecture or other bus or mesh architectures. While a single bus is illustrated, it is to be appreciated that computer 800 may communicate with various devices, circuits, logics, and peripherals using other buses that are not illustrated (e.g., PCIE, SATA, Infiniband, 1394, USB, Ethernet).

Computer 800 may interact with input/output devices via I/O interfaces 818 and input/output ports 810. Input/output devices can include, but are not limited to, CT systems, MRI systems, digital whole slide scanners, an optical microscope, a keyboard, a microphone, a pointing and selection device, cameras, video cards, displays, disk 806, network devices 820, or other devices. Input/output ports 810 can include but are not limited to, serial ports, parallel ports, or USB ports.

Computer 800 may operate in a network environment and thus may be connected to network devices 820 via I/O interfaces 818 or I/O ports 810. Through the network devices 820, computer 800 may interact with a network. Through the network, computer 800 may be logically connected to remote computers. The networks with which computer 800 may interact include, but are not limited to, a local area network (LAN), a wide area network (WAN), or other networks, including the cloud.

Examples herein can include subject matter such as an apparatus, a personalized medicine system, a CADx system, a processor, a system, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system for predicting patient response to immunotherapy according to embodiments and examples described.

One example embodiment includes a computer-readable storage device storing computer-executable instructions that, in response to execution, cause a personalized medicine system or processor to perform operations. The operations include accessing a pre-treatment image of a region of tissue demonstrating NSCLC. The pre-treatment image represents a tumor or lung nodule located in the region of tissue. The pre-treatment image includes a plurality of voxels, a voxel having an intensity value.

The operations also include annotating the tumor represented in the pre-treatment image. In one embodiment, the tumor represented in the pre-treatment image may be annotated using 3D Slicer software, or may be annotated automatically. Annotating the tumor may include segmenting the tumor from the background of the image or from other, non-tumor tissue represented in the image. Machine learning tumor segmentation techniques may be employed.

The operations also include accessing at least one post-treatment image of the region of tissue demonstrating NSCLC. The at least one post-treatment image represents the tumor represented in the pre-treatment image. The at least one post-treatment image includes a plurality of voxels. A voxel has an intensity value.

The operations also include annotating the tumor represented in the at least one post-treatment image. In one embodiment, the tumor represented in the at least one post-treatment image may be annotated using 3D Slicer software, or may be annotated automatically. Annotating the tumor may include segmenting the tumor from the background of the at least one post-treatment image or from other, non-tumor tissue represented in the image. Machine learning tumor segmentation techniques may be employed.

The operations also include generating a registered image by registering the pre-treatment image with the at least one post-treatment image. In one embodiment, the registered image is generated using affine registration. In another embodiment, the operations may include other registration approaches, including a rigid registration approach, or a deformable registration approach.

The operations also include extracting a set of pre-treatment radiomic features from the registered image. In one embodiment, the set of pre-treatment radiomic features includes a Sobel y gradient feature, a Laws gradient x feature, a Laws E3L3E3 feature, a Sobel yz gradient feature, a Laws L3S3E3 feature, and a Laws E5S5L5 feature. In another embodiment, other, different radiomic features may be selected.

The operations also include extracting a set of post-treatment radiomic features from the registered image. In one embodiment, the set of post-treatment radiomic features includes a Sobel y gradient feature, a Laws gradient x feature, a Laws E3L3E3 feature, a Sobel yz gradient feature, a Laws L3S3E3 feature, and a Laws E5S5L5 feature. In another embodiment, other, different radiomic features may be selected. For example, other, different texture features, intensity features, or shape features may be extracted from the registered image. While six radiomic features are extracted in this embodiment, in another embodiment, other, different numbers of radiomic features may be extracted. In one embodiment, the operations further include normalizing the set of pre-treatment radiomic features and the set of post-treatment radiomic features.

The operations also include generating a set of delta radiomic features by computing, on a per-voxel basis, a difference between the set post-treatment radiomic features and the set of pre-treatment radiomic features. In one embodiment, the operations further include selecting the set of delta radiomic features based, at least in part, on a level of stability of a delta radiomic feature.

The operations also include providing the set of delta radiomic features to a machine learning classifier. The machine learning classifier may be an SVM, a QDA classifier, an LDA classifier, a random forests classifier, a CNN, or other type of machine learning classifier. In one embodiment, the operations further include training the machine learning classifier. In one embodiment, the operations further include testing the machine learning classifier on a held-out testing dataset.

The operations also include receiving, from the machine learning classifier, a probability that the region of tissue will respond to immunotherapy. The probability is computed based, at least in part, on the set of delta radiomic features.

The operations also include classifying the region of tissue as a responder or non-responder based, at least in part, on the probability. In one embodiment, the region of tissue is classified as a responder when the probability has a value of 0.5 or greater. In another embodiment, the region of tissue is classified as a responder when the probability has another, different value.

The operations further include generating an NSCLC immunotherapy treatment plan. The NSCLC immunotherapy treatment plan is based, at least in part, on the classification and at least one of the probability, the set of delta radiomic features, the pre-treatment image, or the at least one post-treatment image. In one embodiment, the operations further include controlling an immunotherapy dosage system to administer a dosage of an immunotherapy agent defined by the NSCLC immunotherapy plan by an intravenous infusion, an intravesical infusion, or other technique.

In one embodiment, the operations further include controlling a personalized medicine system, a CADx system, or processor to display the NSCLC immunotherapy treatment plan, the probability, the classification, the set of delta radiomic features, the registered image, the at least one post-treatment image, or the pre-treatment image, on a computer monitor, a smartphone display, a tablet display, or other displays.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. An apparatus for predicting patient response to immunotherapy, the apparatus comprising:
    a processor;
    a memory that stores a digitized computed tomography (CT) pre-treatment image and at least one digitized CT post-treatment image of a region of tissue demonstrating non-small cell lung cancer (NSCLC), where the region of tissue includes a tumor, the pre-treatment image having a plurality of voxels and the at least one post-treatment image having a plurality of voxels, where a voxel has an intensity value;
    an input/output (I/O) interface;
    a set of circuits comprising an image acquisition circuit, a segmentation and registration circuit, a feature extraction circuit, a delta radiomics circuit, a classification circuit, and a personalized medicine circuit; and
    an interface to connect the processor, the memory, the I/O interface and the set of circuits;
    the image acquisition circuit configured to access the pre-treatment image and the at least one post-treatment image;
    the segmentation and registration circuit configured to annotate the tumor represented in the pre-treatment image, to annotate the tumor represented in the at least one post-treatment image, and to generate a registered image by registering the pre-treatment image with the at least one post-treatment image;
    the feature extraction circuit configured to select a set of pre-treatment radiomic features from the registered image and to select a set of post-treatment radiomic features from the registered image;
    the delta radiomics circuit configured to generate a set of delta radiomic features by computing a difference between the set of post-treatment radiomic features and the set of pre-treatment radiomic features and to provide the set of delta radiomic features to the classification circuit;
    the classification circuit configured to generate a probability that the region of tissue will respond to immunotherapy based, at least in part, on the set of delta radiomic features, and to classify the region of tissue as a responder or non-responder based, at least in part, on the probability; and
    a personalized medicine circuit configured to generate an NSCLC immunotherapy treatment plan based, at least in part, on the classification and at least one of the probability, the set of delta radiomic features, the pre-treatment image, or the at least one post-treatment image.

2. The apparatus of claim 1, where the segmentation and registration circuit registers the pre-treatment image with the at least one post-treatment image using an affine registration approach, a rigid registration approach, or a deformable registration approach.

3. The apparatus of claim 1, where the feature extraction circuit selects the set of pre-treatment radiomic features and the set of post-treatment radiomic features based on a threshold level of reliability and a threshold level of reproducibility, where the feature extraction circuit computes the threshold level of reliability and the threshold level of reproducibility using a concordance correlation coefficient (CCC) approach.

4. The apparatus of claim 3, where the set of pre-treatment radiomic features includes a Sobel y gradient feature, a Laws gradient x feature, a Laws E3L3E3 feature, a Sobel yz gradient feature, a Laws L3S3E3 feature, and a Laws E5S5L5 feature, and where the set of post-treatment radiomic features includes a Sobel y gradient feature, a Laws gradient x feature, a Laws E3L3E3 feature, a Sobel yz gradient feature, a Laws L3S3E3 feature, and a Laws E5S5L5 feature.

5. The apparatus of claim 1, where the feature extraction circuit is further configured to normalize the set of pre-treatment radiomic features and the set of post-treatment radiomic features.

6. The apparatus of claim 1, where the delta radiomics circuit generates the set of delta radiomic features on a per-voxel basis.

7. The apparatus of claim 1, where the classification circuit includes a machine learning classifier, where the machine learning classifier is a support vector machine (SVM) having three kernels, where the three kernels include a linear kernel, a radial basis function (RBF) kernel, and a polynomial kernel, or where the machine learning classifier is one of a discriminant analysis (DA) classifier, a nearest neighbor (NN) classifier, a convolutional neural network (CNN), or a random forest (RF) classifier.

8. The apparatus of claim 1, where the NSCLC immunotherapy treatment plan defines an immunotherapy drug dosage amount and an immunotherapy drug dosage schedule.

9. The apparatus of claim 1, further comprising a training circuit configured to train the classification circuit, where the training circuit:
accesses a dataset of CT images of a region of tissue demonstrating NSCLC, where a first member of the dataset is a pre-treatment image, and a second member of the dataset is a post-treatment image of the region represented in the first member;
selects a set of training delta radiomic features from the dataset, where the set of training delta radiomic features includes a feature selected from the first member, and a corresponding feature selected from the associated second member, where the set of training delta radiomic features is selected based on a level of discriminability and on a level of stability, where the level of stability is computed using a concordance correlation coefficient (CCC) approach; and
trains the classification circuit using the set of training delta radiomic features.

10. A non-transitory computer-readable storage device storing computer-executable instructions that when executed by a computer controls the computer to perform a method for predicting non-small cell lung cancer (NSCLC) patient response to immunotherapy, the method comprising:
accessing a pre-treatment image of a region of tissue in a patient demonstrating NSCLC, where the pre-treatment image includes a plurality of voxels;
annotating a tumor represented in the pre-treatment image;
accessing at least one post-treatment image of the region of tissue demonstrating NSCLC, where the at least one post-treatment image includes the tumor, and where the post-treatment image includes a plurality of voxels;
annotating the tumor represented in the at least one post-treatment image;
generating a registered image by registering the pre-treatment image with the at least one post-treatment image;
extracting a set of pre-treatment radiomic features from the registered image;
extracting a set of post-treatment radiomic features from the registered image;
generating a set of delta radiomic features by computing, on a per-voxel basis, a difference between the set of post-treatment radiomic features and the set of pre-treatment radiomic features;
providing the set of delta radiomic features to a machine learning classifier;
receiving, from the machine learning classifier, a probability that the region of tissue will respond to immunotherapy based, at least in part, on the set of delta radiomic features;
classifying the region of tissue as a responder or non-responder based, at least in part, on the probability; and
generating an NSCLC immunotherapy treatment plan based, at least in part, on the classification and at least one of the probability, the set of delta radiomic features, the pre-treatment image, or the at least one post-treatment image.

11. The non-transitory computer-readable storage device of claim 10, where the pre-treatment image is a computed tomography (CT) image of a first patient.

12. The non-transitory computer-readable storage device of claim 11, where the at least one post-treatment image is a CT image of the first patient.

13. The non-transitory computer-readable storage device of claim 12, where the at least one post-treatment image is acquired at least a first time interval after the pre-treatment image.

14. The non-transitory computer-readable storage device of claim 13, where the first time interval is two weeks.

15. The non-transitory computer-readable storage device of claim 10, where registering the pre-treatment image with the at least one post-treatment image includes registering the pre-treatment image with the at least one post-treatment image using an affine registration approach, a rigid registration approach, or a deformable registration approach.

16. The non-transitory computer-readable storage device of claim 10, the method further comprising normalizing the set of pre-treatment radiomic features and the set of post-treatment radiomic features.

17. The non-transitory computer-readable storage device of claim 10, where the set of pre-treatment radiomic features includes a Sobel y gradient feature, a Laws gradient x feature, a Laws E3L3E3 feature, a Sobel yz gradient feature, a Laws L3S3E3 feature, and a Laws E5S5L5 feature, and the set of post-treatment radiomic features includes a Sobel y gradient feature, a Laws gradient x feature, a Laws E3L3E3 feature, a Sobel yz gradient feature, a Laws L3S3E3 feature, and a Laws E5S5L5 feature.

18. The non-transitory computer-readable storage device of claim 10, where the NSCLC immunotherapy treatment plan defines an immunotherapy drug dosage amount and an immunotherapy drug dosage schedule.

19. The non-transitory computer-readable storage device of claim 18, the method further comprising:
controlling a personalized medicine system to display the NSCLC immunotherapy treatment plan, the classification, the probability, the set of delta radiomic features, the pre-treatment image, or the at least one post-treatment image; and
administering the immunotherapy drug to the patient according to the NSCLC immunotherapy treatment plan.

20. The non-transitory computer-readable storage device of claim 10, the method further comprising training the machine learning classifier.

21. The non-transitory computer-readable storage device of claim 20, where training the machine learning classifier includes:
accessing a set of CT images of a population of NSCLC patients, where the population includes a set of responders and a set of non-responders, where a member of the set of CT images includes a voxel, where the set of CT images includes at least one pre-treatment image associated with a responder member of the population and at least one post-treatment image associated with the responder member, and at least one pre-treatment image associated with a non-responder member of the population and at least one post-treatment image associated with the non-responder member;

dividing the set of CT images into a training set and a testing set, where the training set includes at least one pre-treatment CT image and at least one post-treatment CT image associated with a responder, and at least one pre-treatment CT image and at least one post-treatment CT image associated with a non-responder, and where the testing set includes at least one pre-treatment CT image and at least one post-treatment CT image associated with a responder, and at least one pre-treatment CT image and at least one post-treatment CT image associated with a non-responder;

extracting a set of training pre-treatment radiomic features and a set of training post-treatment radiomic features from the training set;

generating a set of training delta radiomic features by computing, on a per-voxel basis, a difference between the set of training post-treatment radiomic features and the set of training pre-treatment radiomic features;

identifying a set of stable delta radiomic features in the set of training delta radiomic features, where the set of stable delta radiomic features are selected based on a threshold level of reliability and a threshold level of reproducibility using a concordance correlation coefficient (CCC) approach; and training the machine learning classifier using the set of stable delta radiomic features.

22. The non-transitory computer-readable storage device of claim 21, the method further comprising testing the machine learning classifier using the testing set.

23. The non-transitory computer-readable storage device of claim 10, where the machine learning classifier is a support vector machine (SVM).

24. The non-transitory computer-readable storage device of claim 23, where the SVM has three kernels, where the three kernels include a linear kernel, a radial basis function (RBF) kernel, and a polynomial kernel.

25. The non-transitory computer-readable storage device of claim 10, where the machine learning classifier is a discriminant analysis (DA) classifier, a nearest neighbor (NN) classifier, a convolutional neural network (CNN), or a random forest (RF) classifier.

26. The non-transitory computer-readable storage device of claim 10, where the set of pre-treatment radiomic features and the set of post-treatment radiomic features are selected using a minimum redundancy maximum relevance (mRMR) approach, a T-test approach, or a Wilcoxon rank sum test.

27. The non-transitory computer-readable storage device of claim 26, where the set of delta radiomic features are selected based on a threshold level of reliability and a threshold level of reproducibility.

28. The non-transitory computer-readable storage device of claim 27, where the threshold level of reliability and the threshold level of reproducibility are computed using a concordance correlation coefficient (CCC) approach.

29. A non-transitory computer-readable storage device storing computer-executable instructions that, in response to execution, cause a personalized medicine system to perform operations comprising:

accessing a pre-treatment image of a region of tissue demonstrating NSCLC, where the pre-treatment image includes a tumor, where the pre-treatment image includes a plurality of voxels;

annotating the tumor represented in the pre-treatment image;

accessing at least one post-treatment image of the region of tissue demonstrating NSCLC, where the at least one post-treatment image includes the tumor, where the post-treatment image includes a plurality of voxels;

annotating the tumor represented in the at least one post-treatment image;

generating a registered image by registering the pre-treatment image with the at least one post-treatment image;

extracting a set of pre-treatment radiomic features from the registered image;

extracting a set of post-treatment radiomic features from the registered image;

generating a set of delta radiomic features by computing a difference between the set of post-treatment radiomic features and the set of pre-treatment radiomic features, where a member of the set of delta radiomic features has a threshold level of stability;

providing the set of delta radiomic features to a machine learning classifier;

receiving, from the machine learning classifier, a probability that the region of tissue will respond to immunotherapy based, at least in part, on the set of delta radiomic features;

classifying the region of tissue as a responder or non-responder based, at least in part, on the probability; and generating an NSCLC immunotherapy treatment plan based, at least in part, on the classification and at least one of the probability, the set of delta radiomic features, the pre-treatment image, or the at least one post-treatment image.

* * * * *

UNITED STATES PATENT AND TRADEMARK OFFICE
CERTIFICATE OF CORRECTION

PATENT NO.          : 10,575,774 B2
APPLICATION NO.     : 15/853133
DATED               : March 3, 2020
INVENTOR(S)         : Anant Madabhushi et al.

Page 1 of 1

It is certified that error appears in the above-identified patent and that said Letters Patent is hereby corrected as shown below:

In the Specification

Column 1, Line 4, insert the following:
--This invention was made with government support under grants CA179327, CA195152, DK098503, CA199374, CA202752, CA208236, and RR012463 awarded by the National Institutes of Health; and grants W81XWH-16-1-0329, W81XWH-14-1-0323, W81XWH-13-1-0418, and W81XWH-15-1-0558 awarded by the Department of Defense. The government has certain rights in the invention.--

Signed and Sealed this
Fourteenth Day of September, 2021

Drew Hirshfeld
*Performing the Functions and Duties of the*
*Under Secretary of Commerce for Intellectual Property and*
*Director of the United States Patent and Trademark Office*